United States Patent
Ryan

(10) Patent No.: US 12,257,414 B2
(45) Date of Patent: *Mar. 25, 2025

(54) UNIVERSAL CAP FOR MALE AND FEMALE CONNECTORS

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 97 days.

This patent is subject to a terminal disclaimer.

(21) Appl. No.: 17/992,169

(22) Filed: Nov. 22, 2022

(65) Prior Publication Data

US 2023/0080687 A1 Mar. 16, 2023

Related U.S. Application Data

(62) Division of application No. 16/774,853, filed on Jan. 28, 2020, now Pat. No. 11,511,100.

(Continued)

(51) Int. Cl.
*A61M 39/16* (2006.01)
*A01N 47/44* (2006.01)
(Continued)

(52) U.S. Cl.
CPC .......... *A61M 39/162* (2013.01); *A01N 47/44* (2013.01); *A61M 39/20* (2013.01); *A61M 2039/1033* (2013.01)

(58) Field of Classification Search
CPC ................ A61M 39/162; A61M 39/20; A61M 2039/1033; A61M 39/16

See application file for complete search history.

(56) References Cited

U.S. PATENT DOCUMENTS

| 3,403,679 A | 10/1968 | Sinclair et al. |
| 4,417,890 A | 11/1983 | Dennehey et al. |

(Continued)

FOREIGN PATENT DOCUMENTS

| CA | 2523133 C | 2/2013 |
| CN | 101980746 A | 2/2011 |

(Continued)

OTHER PUBLICATIONS

"Final Office Action in U.S. Appl. No. 16/253,683, mailed on Dec. 23, 2020, 9 pages".

(Continued)

*Primary Examiner* — Bradley J Osinski
(74) *Attorney, Agent, or Firm* — Servilla Whitney LLC

(57) ABSTRACT

A cap is described for connection to a medical connector, the cap includes a housing having a top wall and sidewall forming a cavity, and an integrally formed protrusion. The protrusion includes an inner thread on an inner surface, the inner thread being sufficient to interlock with a mating feature of a female needleless connector. The inner surface of the protrusion defines a second cavity. The outer surface of the sidewall of the protrusion is tapered and adapted to engage a male luer connector in a press-fit connection. The second cavity configured to define a chamber to contain an absorbent material and disinfectant or antimicrobial agent. The cap may also include a peel seal to prevent the disinfectant or the antimicrobial agent from exiting the second cavity. An exterior sidewall surface of the housing may include a plurality of grip members.

20 Claims, 13 Drawing Sheets

Related U.S. Application Data

(60) Provisional application No. 62/798,624, filed on Jan. 30, 2019.

(51) Int. Cl.
*A61M 39/10* (2006.01)
*A61M 39/20* (2006.01)

(56) References Cited

U.S. PATENT DOCUMENTS

| | | | |
|---|---|---|---|
| 4,597,758 | A | 7/1986 | Aalto et al. |
| 4,711,363 | A | 12/1987 | Marino |
| 4,738,376 | A | 4/1988 | Markus |
| 5,496,288 | A | 3/1996 | Sweeny |
| 5,676,406 | A | 10/1997 | Simmons et al. |
| 5,755,696 | A | 5/1998 | Caizza |
| 6,632,199 | B1 | 10/2003 | Tucker et al. |
| 7,083,605 | B2 | 8/2006 | Miyahara |
| 8,388,894 | B2 | 3/2013 | Colantonio |
| 8,647,308 | B2 | 2/2014 | Solomon et al. |
| 8,715,231 | B2 | 5/2014 | Woehr |
| 8,721,627 | B2 | 5/2014 | Alpert et al. |
| 8,777,504 | B2 | 7/2014 | Shaw et al. |
| 8,784,388 | B2 | 7/2014 | Charles et al. |
| 8,961,475 | B2 | 2/2015 | Solomon et al. |
| 9,039,989 | B2 | 3/2015 | Lui et al. |
| 9,132,223 | B1 | 9/2015 | Wakeel |
| 9,192,449 | B2 | 11/2015 | Kerr et al. |
| 10,099,048 | B2 | 10/2018 | Chiu et al. |
| 10,166,381 | B2 | 1/2019 | Gardner et al. |
| 10,376,686 | B2 | 8/2019 | Burkholz et al. |
| 10,589,063 | B2 | 3/2020 | Hitchcock et al. |
| 10,603,481 | B2 | 3/2020 | Avula et al. |
| 10,871,246 | B2 | 12/2020 | Marici et al. |
| 11,353,147 | B2 | 6/2022 | Marici |
| 11,511,100 | B2 | 11/2022 | Ryan |
| 11,628,288 | B1 | 4/2023 | Solomon et al. |
| 2003/0209681 | A1 | 11/2003 | Leinsing et al. |
| 2004/0039341 | A1 | 2/2004 | Ranalletta |
| 2004/0044318 | A1 | 3/2004 | Fiser et al. |
| 2005/0147525 | A1 | 7/2005 | Bousquet |
| 2005/0197646 | A1 | 9/2005 | Connell et al. |
| 2007/0060904 | A1 | 3/2007 | Vedrine et al. |
| 2008/0010766 | A1 | 1/2008 | Kaufman et al. |
| 2008/0177250 | A1 | 7/2008 | Howlett et al. |
| 2010/0000040 | A1 | 1/2010 | Shaw et al. |
| 2010/0003067 | A1* | 1/2010 | Shaw ............... A61M 35/006 401/206 |
| 2010/0049170 | A1 | 2/2010 | Solomon et al. |
| 2010/0050351 | A1 | 3/2010 | Colantonio et al. |
| 2010/0100056 | A1 | 4/2010 | Cawthon et al. |
| 2011/0046603 | A1 | 2/2011 | Felsovalyi et al. |
| 2011/0054440 | A1 | 3/2011 | Lewis |
| 2011/0264037 | A1 | 10/2011 | Foshee et al. |
| 2012/0039764 | A1 | 2/2012 | Solomon et al. |
| 2012/0123386 | A1 | 5/2012 | Tsals |
| 2012/0302997 | A1 | 11/2012 | Gardner et al. |
| 2013/0085474 | A1 | 4/2013 | Charles et al. |
| 2013/0171030 | A1 | 7/2013 | Ferlic et al. |
| 2013/0197485 | A1 | 8/2013 | Gardner et al. |
| 2013/0338644 | A1 | 12/2013 | Solomon et al. |
| 2014/0052074 | A1 | 2/2014 | Tekeste |
| 2014/0150832 | A1 | 6/2014 | Rogers et al. |
| 2014/0366914 | A1 | 12/2014 | Kerr et al. |
| 2015/0011936 | A1 | 1/2015 | Okihara et al. |
| 2015/0094666 | A1 | 4/2015 | Bates et al. |
| 2016/0045629 | A1 | 2/2016 | Gardner et al. |
| 2016/0067422 | A1 | 3/2016 | Davis et al. |
| 2017/0203087 | A1 | 7/2017 | Ryan et al. |
| 2017/0203092 | A1 | 7/2017 | Ryan et al. |
| 2018/0085568 | A1 | 3/2018 | Drmanovic |
| 2018/0200145 | A1 | 7/2018 | Sanders et al. |
| 2018/0200500 | A1 | 7/2018 | Ziebol et al. |
| 2018/0214684 | A1 | 8/2018 | Avula et al. |
| 2018/0243547 | A1 | 8/2018 | Fox et al. |
| 2018/0256883 | A1 | 9/2018 | Follman et al. |
| 2019/0001115 | A1 | 1/2019 | Ma et al. |
| 2019/0151643 | A1 | 5/2019 | Alpert |
| 2019/0234540 | A1 | 8/2019 | Marici et al. |
| 2019/0308006 | A1 | 10/2019 | Erekovcanski et al. |
| 2019/0351212 | A1 | 11/2019 | Dudar et al. |
| 2020/0147360 | A1 | 5/2020 | Arnett et al. |
| 2021/0100996 | A1 | 4/2021 | Wijesuriya et al. |
| 2021/0187267 | A1 | 6/2021 | Jiang |
| 2022/0273931 | A1 | 9/2022 | Jiang et al. |
| 2023/0080687 | A1 | 3/2023 | Ryan |

FOREIGN PATENT DOCUMENTS

| | | |
|---|---|---|
| CN | 102448502 A | 5/2012 |
| CN | 204161736 U | 2/2015 |
| CN | 216022674 U | 3/2022 |
| CN | 110090354 B | 1/2023 |
| DE | 20017013 U1 | 12/2000 |
| DE | 10247963 A1 | 5/2004 |
| EP | 2606930 A1 | 6/2013 |
| EP | 2832391 B1 | 1/2018 |
| EP | 3275490 A1 | 1/2018 |
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008253775 A | 10/2008 |
| JP | 2009526241 A | 7/2009 |
| JP | 2010527276 A | 8/2010 |
| JP | 2012522593 A | 9/2012 |
| JP | 2013509274 A | 3/2013 |
| JP | 2014528288 A | 10/2014 |
| JP | 2015517377 A | 6/2015 |
| JP | 2016511111 A | 4/2016 |
| JP | 2016511119 A | 4/2016 |
| JP | 2016104214 A | 6/2016 |
| JP | 7419237 B2 | 1/2024 |
| WO | 200024442 A1 | 5/2000 |
| WO | 200224551 A1 | 3/2002 |
| WO | 2011066586 A1 | 6/2011 |
| WO | 2012144026 A1 | 10/2012 |
| WO | 2014159346 A1 | 10/2014 |
| WO | 2015127285 A1 | 8/2015 |
| WO | 2015174953 A1 | 11/2015 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |
| WO | 2019212637 A1 | 11/2019 |
| WO | 2020056120 A1 | 3/2020 |
| WO | 2020112767 A1 | 6/2020 |

OTHER PUBLICATIONS

"Final Office Action in U.S. Appl. No. 16/254,747, mailed on Jan. 22, 2021, 15 pages".
"Non-Final Office Action in U.S. Appl. No. 16/378,015, mailed Mar. 30, 2021, 10 pages".
"Non-Final Office Action in U.S. Appl. No. 15/838,461 dated Jul. 24, 2020, 10 pages".
"Non-Final Office Action in U.S. Appl. No. 16/253,683, mailed on Jun. 26, 2020, 9 pages".
"Non-Final Office Action in U.S. Appl. No. 16/254,747, mailed on Aug. 20, 2020, 14 pages".
"Non-Final Office Action in U.S. Appl. No. 16/378,015, mailed on Oct. 30, 2020, 18 pages".
"Non-Final Office Action in U.S. Appl. No. 17/076,102 dated Aug. 24, 2021, 10 pages".
"PCT International Search Report and Written Opinion in PCT/US2020/015535 dated May 4, 2020, 13 pages".

(56) References Cited

OTHER PUBLICATIONS

"PCT International Search Report and Written Opinion in PCT/US2020/041097 dated Oct. 27, 2020, 18 pages".
"PCT International Search Report and Written Opinion in PCT/US2020/041312 dated Oct. 19, 2020, 11 pages".
"PCT International Search Report and Written Opinion in PCT/US2020/044942 dated Oct. 16, 2020, 15 pages".
"PCT International Search Report and Written Opinion in PCT/US2020/044951 dated Oct. 14, 2020, 14 pages".
"PCT International Search Report and Written Opinion in PCT/US2020/057611 dated Feb. 5, 2021, 11 pages".
"PCT International Search Report and Written Opinion in PCT/US2020/065229 dated Mar. 29, 2021, 11 pages".
"PCT International Search Report and Written Opinion in PCT/US2021/027214 dated Jul. 19, 2021, 14 pages".
"PCT International Search Report and Written Opinion in PCT/US2021/027218 dated Jul. 22, 2021, 14 pages".
"PCT International Search Report and Written Opinion in PCT/US2021/027219 dated Oct. 22, 2021, 22 pages".
"PCT International Search Report and Written Opinion in PCT/US2021/027220 dated Jul. 21, 2021, 15 pages".
"PCT Invitation to Pay Additional Fees in PCT/US2021/019546, mailed on Jun. 15, 2021, 17 pages".
"PCT Invitation to Pay Additional Fees in PCT/US2021/027219, mailed on Jul. 22, 2021, 15 pages".
"Ruhof Dry Sponges", Ruhof, Sep. 30, 2016, https://www.ruhof.com/products/ruhof-dry-sponges (Year: 2016).
Final Office Action in U.S. Appl. No. 17/229,173 dated May 22, 2024, 28 pages.
Non-Final Office Action in U.S. Appl. No. 16/923,238 dated Feb. 28, 2024, 18 pages.

* cited by examiner

UNIVERSAL CAP FOR MALE AND FEMALE CONNECTORS

CROSS-REFERENCE TO RELATED APPLICATIONS

This application is a divisional of U.S. patent application Ser. No. 16/774,853, filed on Jan. 28, 2020, now U.S. patent Ser. No. 11/511,100 issued Nov. 29, 2022, which claims priority under 35 U.S.C. § 119(e) to U.S. Provisional Application No. 62/798,624, filed Jan. 30, 2019, the disclosures of which are incorporated herein by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors. Generally, exemplary embodiments of the present disclosure relate to the fields of threaded fitting, including medical caps and medical disinfection caps, and in particular caps and/or disinfection caps for uses with fluid luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are, therefore, limited to the types of connectors to which the cap can be attached. Currently, there are male disinfecting cap devices for disinfecting ISO594-2 type of female threaded fluid luer connectors and there are female disinfecting cap devices for disinfecting ISO594-2 type of male threaded fluid luer connectors. However there is not a singular universal disinfecting cap device with features allowing it to interface with either a male or female type of threaded connectors. Thus, prior disinfecting caps were designed to fit one type of connector only, and were specific to one particular size and/or shape of connector. Thus, there is a need for a disinfecting device capable of accommodating multiple types of connectors, including both male and female connectors, to streamline the disinfecting process.

SUMMARY

One aspect of the present disclosure pertains to a device for connection to a medical connector. A first aspect of the present disclosure relates to a cap including a housing and a protrusion. The housing can include a top wall, an essentially cylindrical sidewall forming a cavity, and an open bottom formed by the cylindrical sidewall with an opening to the cavity within the housing for receiving a hub of a female needleless connector or a male needleless connector. The protrusion is integrally formed with the housing and positioned within the cavity. The protrusion includes a distal wall, an open proximal end, and a sidewall extending proximally from the distal wall toward the open proximal end. In one or more embodiments, the sidewall can include a split-thread protrusion integrally formed with the distal wall. The split-thread protrusion includes an inner surface and an outer surface, the inner surface of the split-thread protrusion defining a second cavity. An inner thread can be included on the inner surface of the protrusion, the inner thread being sufficient to interlock with a mating feature of the female needleless connector. In one or more embodiments, the inner thread has an inclined thread pattern or helical thread pattern. In one or more embodiments, the outer surface of the protrusion being tapered, sized and adapted to engage a male luer connector in a press-fit connection sufficient to interlock with a mating feature of said male needleless connector. In one or more embodiments, the protrusion can include one or more cantilevered prongs separated by one or more respective gaps. In one or more embodiments, at least one of the prongs can be configured to bend to facilitate interference fit between the protrusion and the mating feature of the male needleless connector or female needleless connector. In one or more embodiments, the protrusion can extend essentially from an inner surface of the top wall toward the open bottom of the housing. In one or more embodiments, the protrusion can extend essentially parallel to the sidewall of the housing.

The open bottom having a peripheral ledge extending radially outward from the open bottom defining an end face and an engagement surface. The interior wall surface of the protrusion having one or more threads adapted to engage a female luer connector. The exterior wall surface of the protrusion being tapered, sized and adapted to receive a male luer connector.

A peelable seal can be disposed on the end face of the open bottom of the cap to prevent the disinfectant or the antimicrobial agent from exiting the chamber.

In one or more embodiments, the female luer connector is selected from the group consisting essentially of needle-free connectors, stopcocks, and hemodialysis connectors.

In one or more embodiments, the male connector is an intravenous tubing end or stopcock.

The cap can be made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the cap comprises a polypropylene or polyethylene material. In one or more embodiments, the exterior cap surface includes a plurality of grip members.

In one or more embodiments, the absorbent material has slits. In one or more embodiments, the absorbent material is under radial compression by the inner threads to retain the absorbent material in the chamber. In one or more embodiments, the absorbent material is retained in the chamber without radial compression by the inner threads. In one or more embodiments, the absorbent material is a nonwoven material, foam or a sponge. In a specific embodiment, the foam is a polyurethane foam.

In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material toward the distal wall of the chamber or first cavity or second cavity upon connection to the female luer connector or the male luer connector allows the connector to contact the disinfectant or antimicrobial agent to disinfect the female luer connector or the male luer connector.

In one or more embodiments, the peelable seal comprises an aluminum or multi-layer polymer film peel back top. In a specific embodiment, the peelable seal is heat-sealed or induction sealed to the engagement surface.

A second aspect of the present disclosure pertains to a method of disinfecting a medical connector. The method comprises connecting the device of one or more embodiments to a medical connector, wherein connecting includes engaging the interior wall surface upon insertion into the chamber such that the medical connector contacts the absorbent material and the disinfectant or antimicrobial agent.

A third aspect of the present disclosure pertains to an assembly. The assembly comprises the device of one or more embodiments connected to a medical connector. In one or more embodiments, the medical connector is selected from a male luer connector, a female luer connector, and needleless connector.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Figure 1:
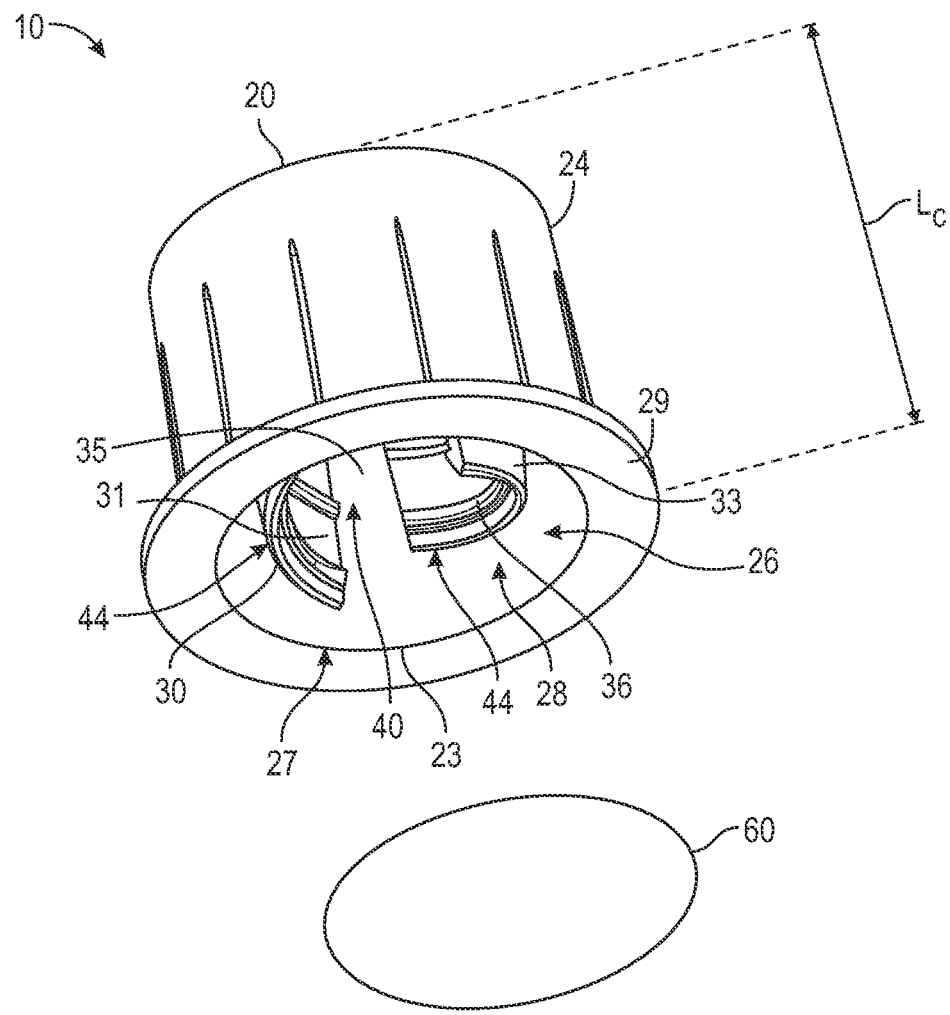
FIG. 1 shows a perspective bottom view of an embodiment of a cap of the present disclosure.

Embodiments of the disclosure pertain to a sterile, universal cap for connection to and disinfection of a medical connector, including male connectors and female connectors. The male connectors and female connectors can be male luer connectors and female luer connectors. Embodiments of the cap comprise a housing having a cavity and a protrusion disposed within the cavity. The cavity defines a closed end, an open bottom and an inner sidewall, the closed end having an external top wall and an internal distal wall. The inner sidewall of the housing having a length $L_C$ extending from the distal wall to the open bottom and defining a chamber. In one or more embodiments, the open bottom includes a peripheral ledge or rim extending radially outward from the open bottom defining an end face and an engagement surface where a peelable seal may be secured. The protrusion has an interior wall surface and an exterior wall surface, the interior wall surface having one or more threads adapted to engage a female luer connector, and the exterior wall surface having a taper from the distal wall, the taper extending in a proximal direction sized and adapted to engage a male luer connector in a press-fit connection sufficient to interlock with a mating feature of said male needleless connector. The cap may further comprise absorbent material, the absorbent material disposed within the chamber. The absorbent material containing a disinfectant or the antimicrobial agent within. The cap provides a mechanical barrier for connectors and retains the antimicrobial agent for disinfection. The cap of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "tip", "hub", "thread", "sponge", "prong", "protrusion", "wall", "top", "side", "bottom" and others are used throughout this specification to facilitate understanding, it is not intended to limit any components that can be used in combinations or individually to implement various aspects of the embodiments of the present disclosure.

As used herein, the term "medical device" refers to common medical devices having threaded or interlocking connections, the connections having corresponding mating elements. By way of example but not limitation, a syringe may have a male threaded connection which releasably interlocks with a secondary medical device such as a male luer connection of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "slant", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide caps that can reduce the number of device types and logistics currently needed in the hospital setting for connecting, capping, and/or disinfecting male and female threaded fluid luer connectors, by roughly half by including in a single cap or device features allowing it to be use with both male needleless connectors and female needleless connectors.

In one or more exemplary embodiments of present disclosure, a cap, connector cap or disinfecting cap includes tapered surfaces, integrated thread(s), and other features in any and all combinations allowing it to interface with both male needless connectors and female needless connectors, wherein the tapered surfaces secure the male needleless connector with a press-fit between the tapered surface of the cap and a corresponding tapered surface of the male needless connector, and the integrated threads engage corresponding threads of the female needleless connector.

According to further exemplary implementations of the embodiments of the present disclosure, configuration of structural elements making up the cap include one or more cantilevered prongs disposed in cap's inner cavity, the cantilevered prongs comprising an inner thread to connect to female needleless connectors and an outer tapered surface to connect to male needleless connectors, to facilitate securing of the cap onto a female fitting or onto a male fitting, respectively.

According to still further exemplary implementations of the embodiments of the present disclosure, the cantilevered prong may be in the form of protrusion and may be of a split thread type in which the protrusion may elastically deform or bend in order to allow better interference fit compliance with the fittings.

According to still further exemplary implementations of the embodiments of the present disclosure, female threads are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting.

In one or more embodiments, the female needless connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, *Nexus*, InVision, Vadsite, Bionector, etc.

In one or more embodiments, the male connector may be an intravenous tubing end, a stopcock or male lock luer.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Figure 2:
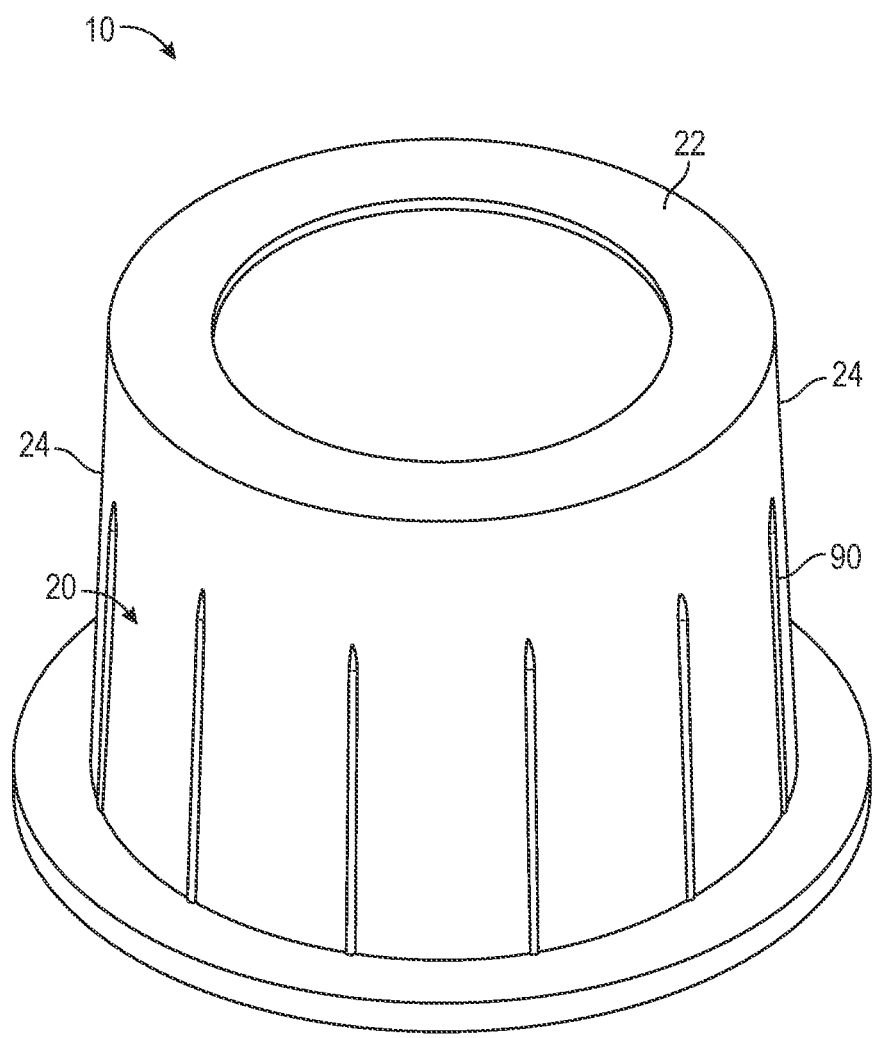
FIG. 2 shows a perspective elevation view of a device according to an embodiment of the present disclosure.
Figure 3:
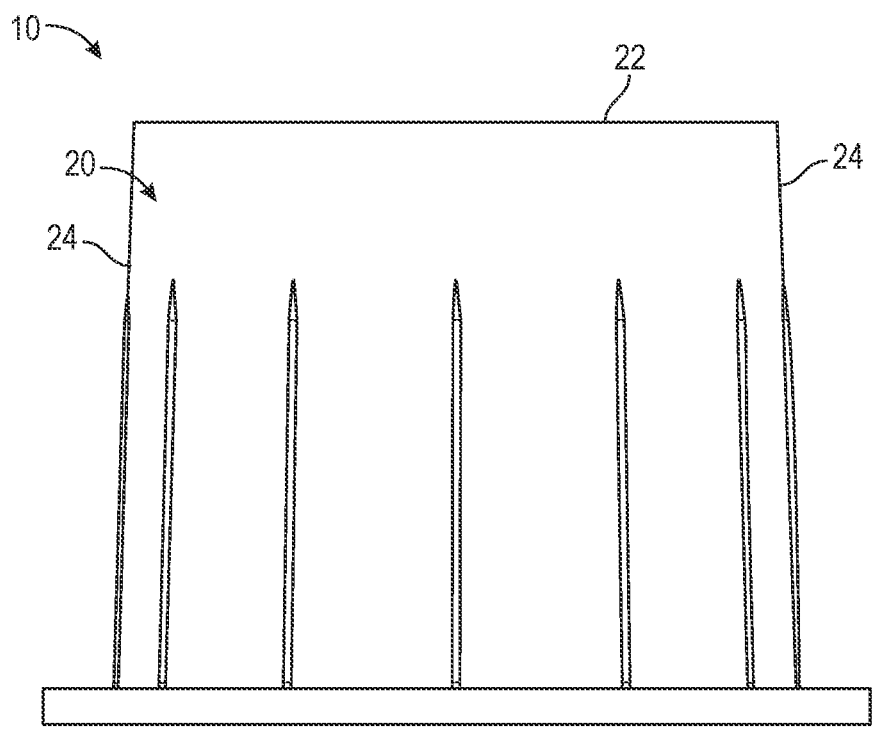
FIG. 3 shows a side view of the cap according to an embodiment of the present disclosure.
Figure 4:
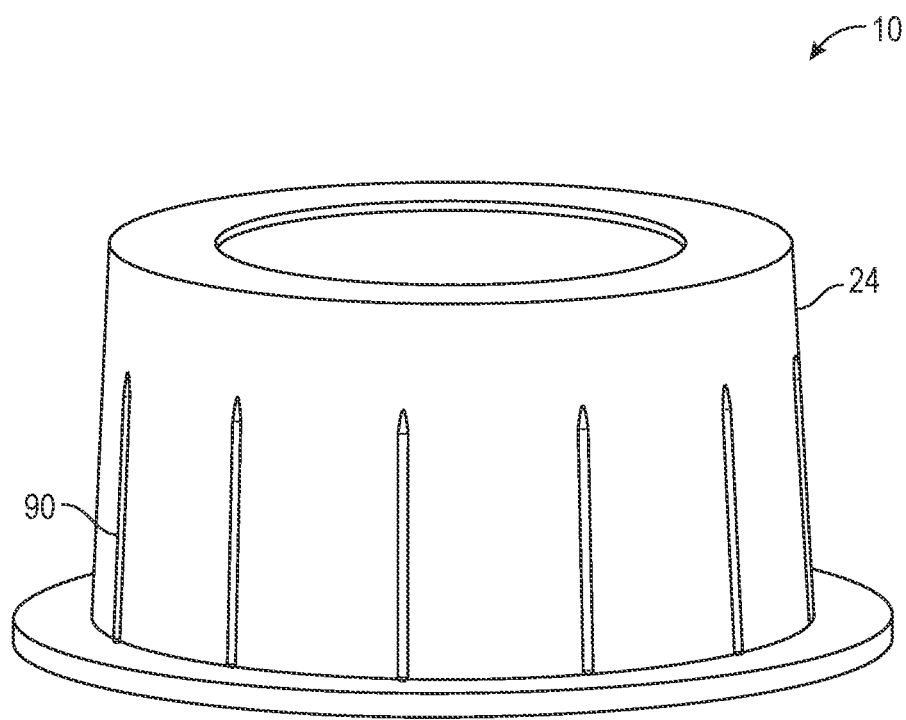
FIG. 4 shows a perspective side view of a component of the device of FIG. 1.
Figure 5:
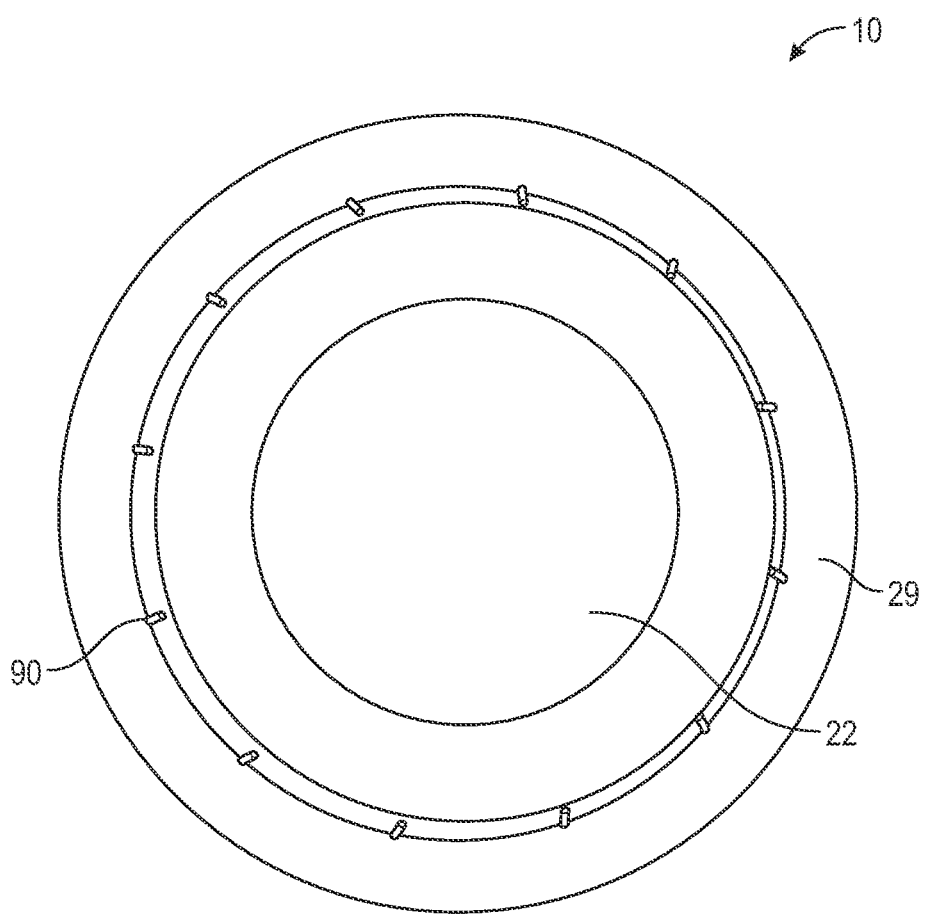
FIG. 5 shows a top view of an embodiment of a cap of the present disclosure.

A first aspect of the present disclosure relates to a cap 10 including a housing 20 and a prong in the form of a protrusion 30. As shown in FIGS. 1-2, housing 20 includes a top wall 22, an outer sidewall 24. an essentially cylindrical inner sidewall 26 forming a first cavity 28, and an open bottom 23 formed by the cylindrical sidewall 26 with an open bottom 23 to the first cavity 28 within the housing 20 for receiving a hub of a female needleless connector or a male needleless connector. In one or more embodiments, the open bottom 23 includes a peripheral ledge or rim 29 extending radially outward from the open bottom 23 defining an end face and an engagement surface where a peelable seal 60 may be secured.

In one embodiment, the protrusion 30 is integrally formed with the housing 20 and is positioned within the first cavity 28. The protrusion 30 extends from the distal wall 25 at least partially the length $L_c$, the protrusion 30 including an inner surface 31 and an outer surface 33, the inner surface 31 of protrusion 30 defining a second cavity 40 disposed within the protrusion 30.

In one or more embodiments, the cap 10 of the present disclosure has inner thread 36 that has a size and pitch to engage a threadable segment of a female connector, such as for example, a female luer connector. Such connectors are generally and commonly used as catheter and other fluid-tight protective connectors in medical applications. In one or more embodiments, cap 10 provides a protective cover for a female luer connector when engaged with the connector when threads from the female luer connector engage and form a releasable connection with inner threads 36 of cap 10. The inner thread 36 can be included on the inner surface 31 of protrusion 30, the inner thread 36 being sufficient to interlock with a mating feature of the female needleless connector. In one or more embodiments, the inner surface 31 of protrusion 30 comprises inner threads 36 running a partial or full length of the inner surface 31 from the distal wall 25 distal wall 25. In one or more embodiments, the thread pattern is inclined. In one or more embodiments, the thread pattern is helical.

The outer surface 33 of the protrusion 30 is tapered, sized and adapted to engage a male luer connector in a press-fit connection sufficient to interlock with a mating feature of said male needleless connector. In one or more embodiments, the protrusion 30 can comprise one or more cantilevered prongs 44 separated by one or more respective gaps 35. In one or more embodiments, at least one of the prongs 44 can be configured to elastically deform or bend to facilitate interference fit between the at least one prongs 44 and the mating feature of the male needleless connector or female needleless connector.

In one or more embodiments, protrusion 30 can extend essentially from the distal wall 25 in a proximal direction toward the open bottom 23 of the housing 20. In one or more embodiments, the protrusion 30 can extend essentially parallel to the inner sidewall 26 of the housing 20.

Referring to FIGS. 2-5, according to exemplary embodiments of the present disclosure, the cap 10 comprises a housing 20, the housing 20 including a top wall 22, and an outer sidewall 24, the outer sidewall 24 being essentially cylindrical. In one or more embodiments, the housing 20 further comprises peripheral ledge or rim 29 extending radially outward from the open bottom 23 defining an end face and an engagement surface where a peelable seal (not shown) may be secured. The exterior surface of the outer sidewall 24 further comprises a plurality of grip members 90, aiding in rotation or handling of the housing 20. The cap 10 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 10 comprises a polypropylene or polyethylene material.

Figure 6:
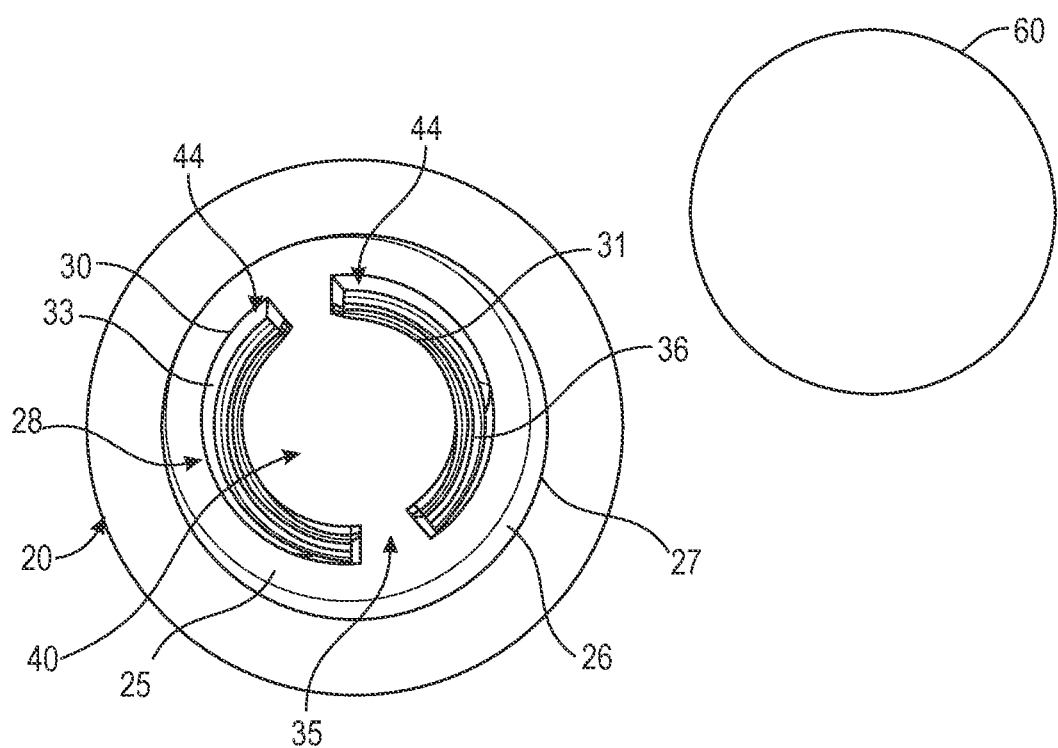
FIG. 6 shows a bottom view of an embodiment of a cap of the present disclosure.
Figure 7:
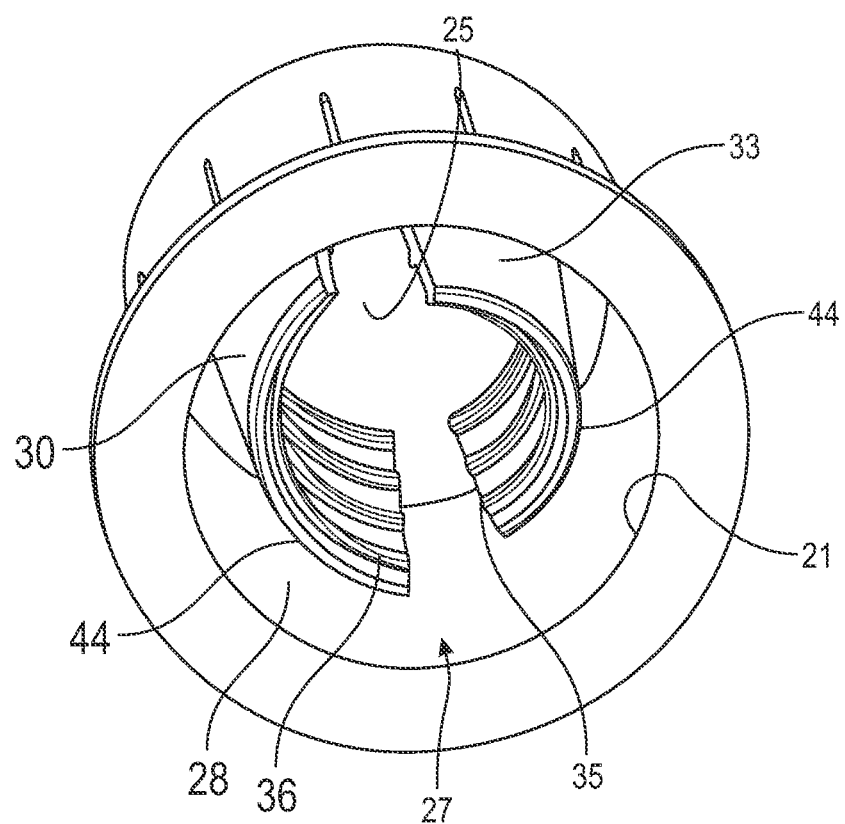
FIG. 7 shows a perspective bottom view of an embodiment of a cap of the present disclosure.
Figure 8:
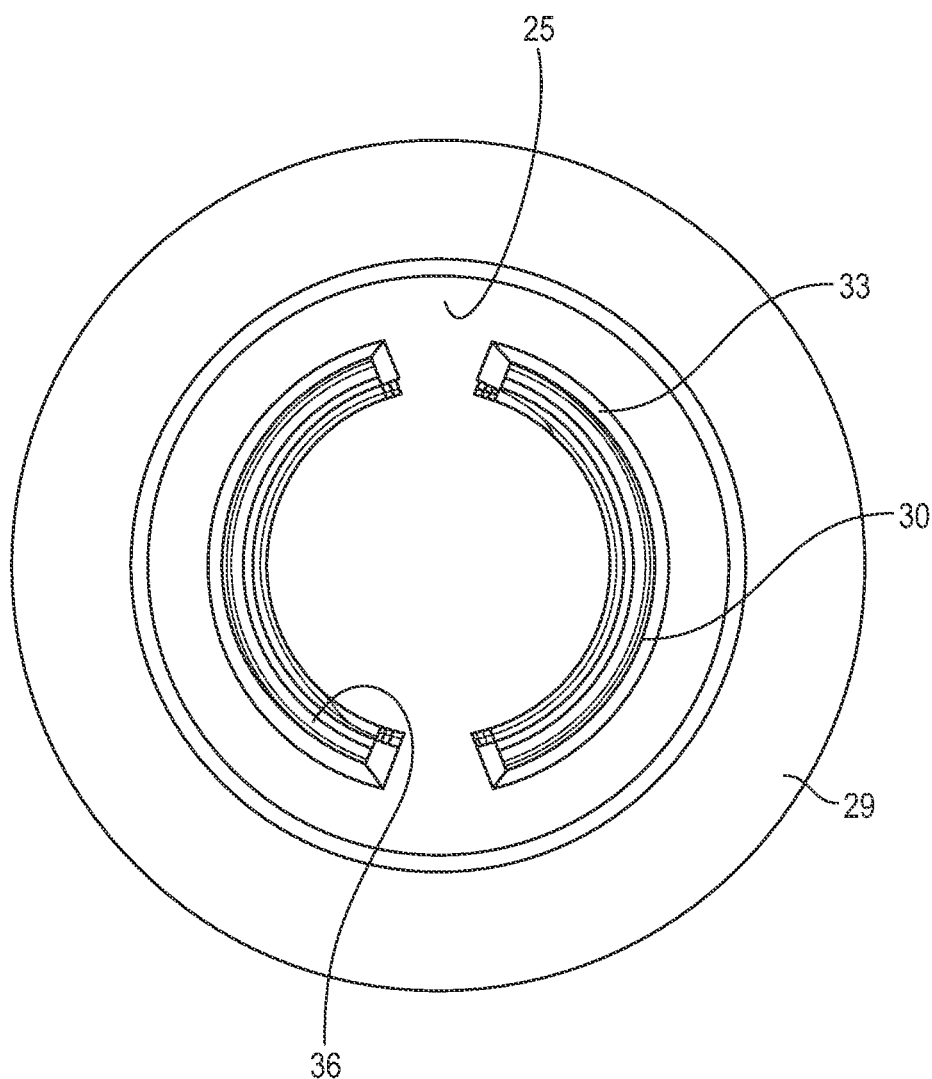
FIG. 8 shows a bottom perspective view of a cap of FIG. 1.

Referring to FIGS. 6-8, according to exemplary embodiments of the present disclosure a cap 10 comprises a housing 20 which includes an inner sidewall 26 and a distal wall 25 defining a first cavity 28, and an open bottom 23 into the first cavity 28. From the distal wall 25 extends a protrusion 30 (which can be essentially cylindrical and coaxial with inner sidewall 26) having an inner surface 31 defining a second cavity 40, and a tapered outer surface 33 defining and outer portion of the first cavity 28. The protrusion 30 comprises an inner thread 36 on its inner surface 31 for engaging a female connector and an outer surface 33 being tapered, sized and adapted to engage a male luer connector in a press-fit connection sufficient to interlock with a mating feature of said male needleless connector. The protrusion 30 is illustrated as comprising two prongs 44 spaced by cutouts or gaps 35 and extending essentially from the distal wall 25 in a proximal direction.

Figure 9:
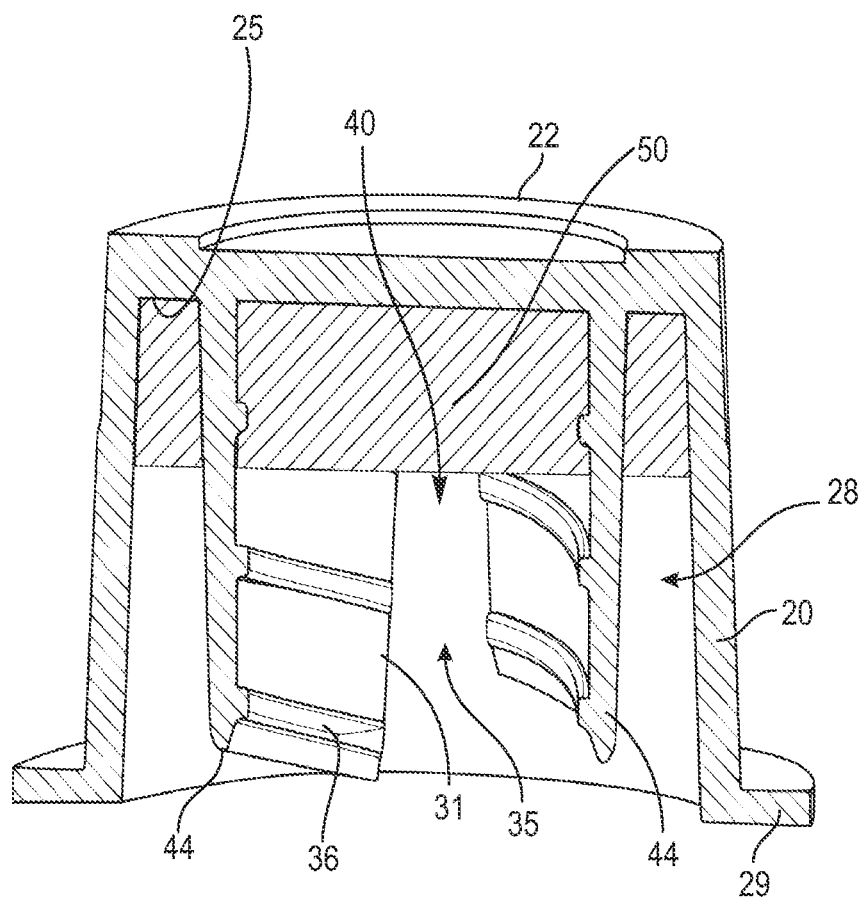
FIG. 9 shows a cross-sectional view of a cap of FIG. 1.

In an exemplary implementation, a peelable seal 60 can be provided to seal the open bottom 23 prior to use of cap 10, for example, by attachment to a surface of a rim 29 of an open bottom 23 of housing 20, as described for example in the above-referenced prior applications. Referring to FIG. 1, in one or more embodiments, the peelable seal 60 is disposed on the engagement surface of open bottom 23 of housing 20 to prevent the disinfectant or the antimicrobial agent from exiting the first cavity 28 and second cavity 40. As shown in FIG. 9, the peelable seal 60 minimizes entry of potential particulate hazard and also provides a substantially impermeable enclosure for the cap 10, providing a leak prevention and protection enclosure, protects the contents contained within the first cavity 28 and the second cavity 40, and/or maintains a sealed, sterilized environment. The peelable seal 60 provides a sufficient seal at a range of temperatures, pressures, and humidity levels.

In one or more embodiments, the peelable seal 60 comprises an aluminum or multi-layer polymer film peel back top. In a specific embodiment, the peelable seal 60 is heat-sealed or induction sealed to the open bottom 23 of the cap. In one or more embodiments, the peelable seal 60 comprises a moisture barrier.

Figure 10:
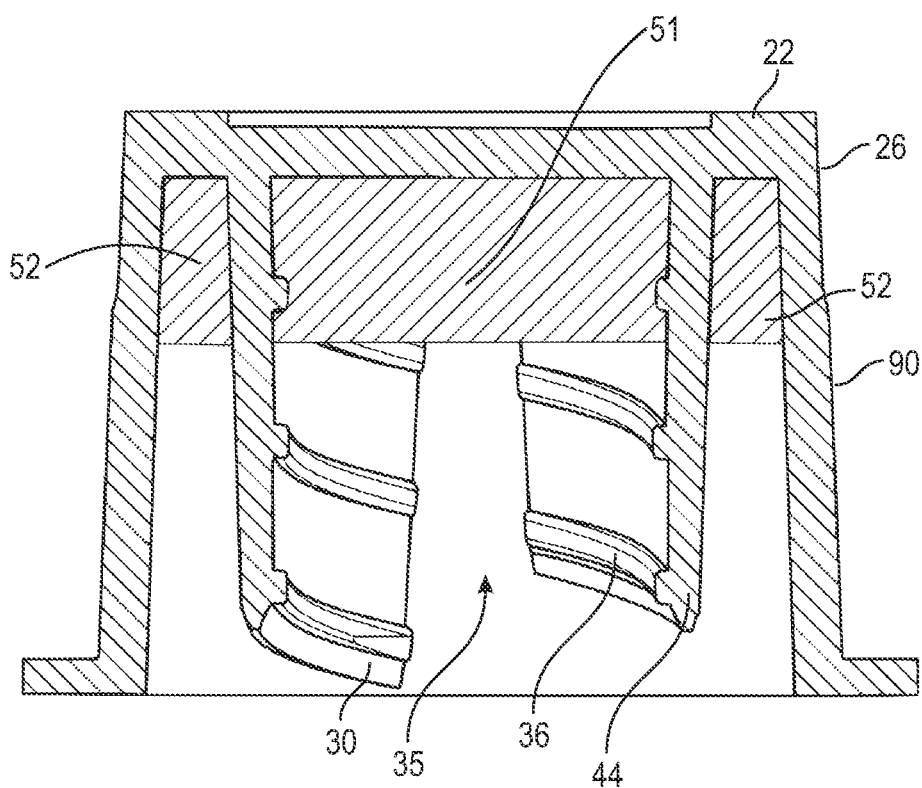
FIG. 10 shows a cross-sectional side view of a cap of FIG. 1.
Figure 11:
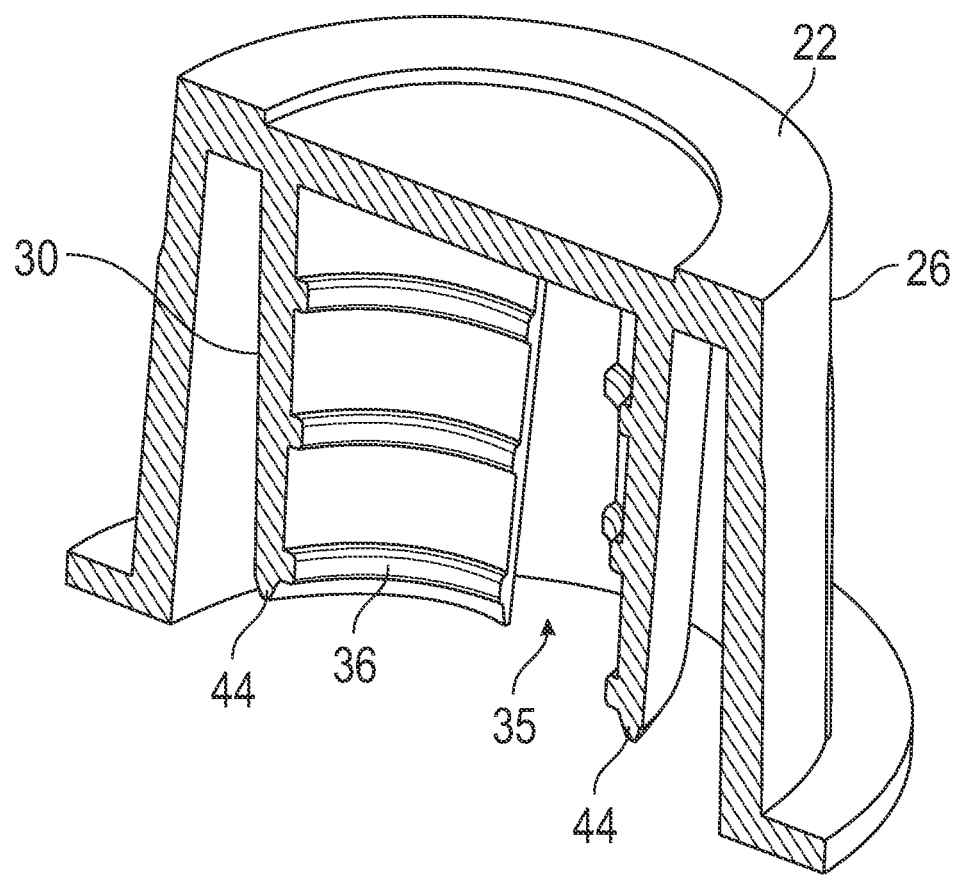
FIG. 11 shows a cross-sectional perspective view of a cap of FIG. 1.

Referring to FIG. 8-11, in one or more embodiments, an absorbent material 50 is disposed within the chamber defined by the first cavity 28 and second cavity 40, the absorbent material being under radial compression by the inner thread 36 on the inner surface 31 of protrusion 30 to retain the absorbent material 50 in the first cavity 28 and second cavity 40. As shown in FIG. 9, the absorbent material 50 may be of a unitary cylindrical shape, having slits through which the prongs 44 of the protrusion 30 may pass through. As shown in FIG. 10, in one or more embodiments, the absorbent material 50 comprises an inner cylindrical material 51 and an outer cylindrical material 52. The inner cylindrical material 51 is disposed within the second cavity 40, and the outer cylindrical material 52 being disposed within the first cavity 28, the outer cylindrical material 52 being a ring having an aperture and an aperture diameter essentially equal to the diameter of the protrusion 30, so that the outer cylindrical material 52 is disposed only within the first cavity 28, being in contact with the inner sidewall 26 of the housing 20 and the outer surface 33 of the protrusion 30. The absorbent material 50, the inner cylindrical material 51 and outer cylindrical material 52 abut the distal wall 25 when placed within the first cavity 28 or second cavity 40.

In one or more embodiments, the absorbent material 50 is a nonwoven material, foam, or a sponge. In a specific embodiment, the foam is a polyurethane foam. In a specific embodiment the absorbent material 50 is in the form of a foam plug. In one or more embodiments, the absorbent material 50 includes one or more slits. With the absorbent material 50 properly inserted into the first cavity 28 and second cavity 40, the peelable seal 60 may be secured to the engagement surface of open bottom 23 of housing 20.

In yet another exemplary implementation, a disinfecting member or members, such as an absorbent material 50, in the form of an IPA soaked sponge and/or sponge. In one or more embodiments, absorbent material 50 can also be formed together as a single cleaning member or separate cleaning member can be provided within first cavity 28.

The cap 10 can achieve disinfection when used on luer connectors by integrating disinfectant or antimicrobial agent in the absorbent material 50, the inner cylindrical material 51 and/or outer cylindrical material 52. The disinfectant or antimicrobial agent can be directly included in the first cavity 28 or second cavity 40 or disinfectant or antimicrobial agent can be absorbed into sponges or foam material that fills the chamber of cap 10. Cap 10 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 50, the inner cylindrical material 51 and/or outer cylindrical material 52 toward the distal wall 25 of housing 20 upon connection to the female luer connector or the male luer connector allows the connector to contact the disinfectant or antimicrobial agent to disinfect the female luer connector or the male luer connector. Thus, compression of the absorbent material disinfects the female luer connector. The absorbent material 50, the inner cylindrical material 51 and/or outer cylindrical material 52 and the disinfectant or the antimicrobial agent contacts the female or male luer connector after insertion of the female or male luer connector into the chamber of the cap.

In an exemplary implementation of embodiments of the present disclosure, protrusion 30 can be cantilevered, for example by having one or more cutouts or gaps 35. In an exemplary implementation, at least a portion of the a cantilevered protrusion 30 may bend in order to allow better interference fit compliance with the fitting such as at least one of male connector or female connector.

In yet another exemplary implementation, protrusion 30 can extend essentially from the distal wall 25 toward the open bottom 23 of housing 20.

In still further exemplary implementation, protrusion 30 can extend essentially parallel to inner sidewall 26.

Figure 12:
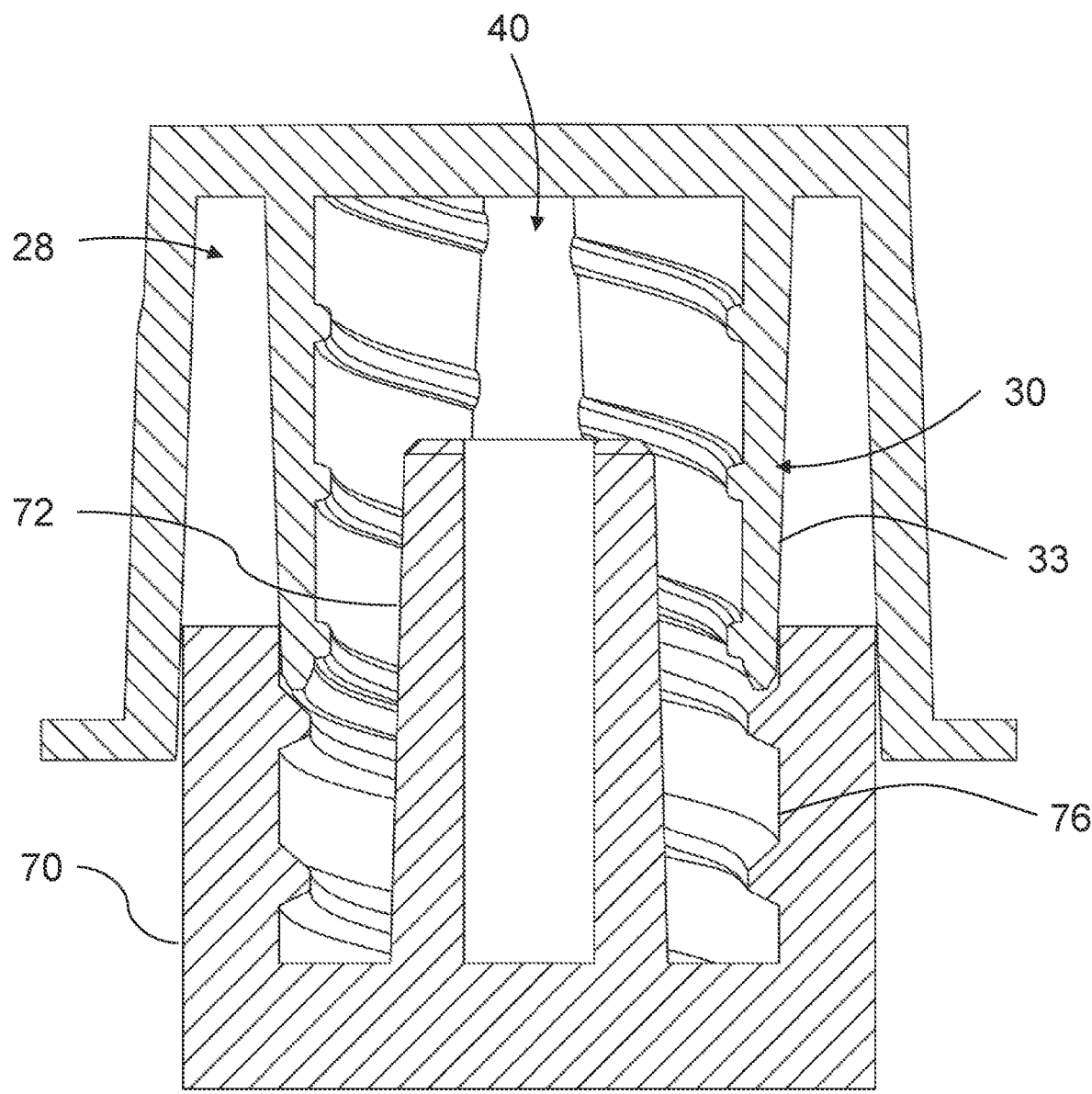
FIG. 12 shows a cross-section prospective view of an exemplary cap engaged into a male needless connector; and, FIG. 13 shows a cross-sectional side view of an exemplary cap engaged into a female needless connector.

Referring to FIG. 12, according to exemplary embodiments of the disclosure, cap 10 can receive a tip or hub 72 of a male needleless connector 70, for example after a peelable seal (not shown) which seals first cavity 28 and second cavity 40 is removed or when the peelable seal (not shown) is pierced. The hub 72 is received within the second cavity 40, while a collar 76 of the male needless connector 70 is received within first cavity 28 secured via a press-fit connection with a corresponding tapered collar of the male connector with an outer surface 33 of first cavity 28. As the male needless connector 70 is advanced further into the first cavity 28 and second cavity 40, the collar 76 cause the protrusion 30 to elastically deform or deflect inwardly.

Figure 13:
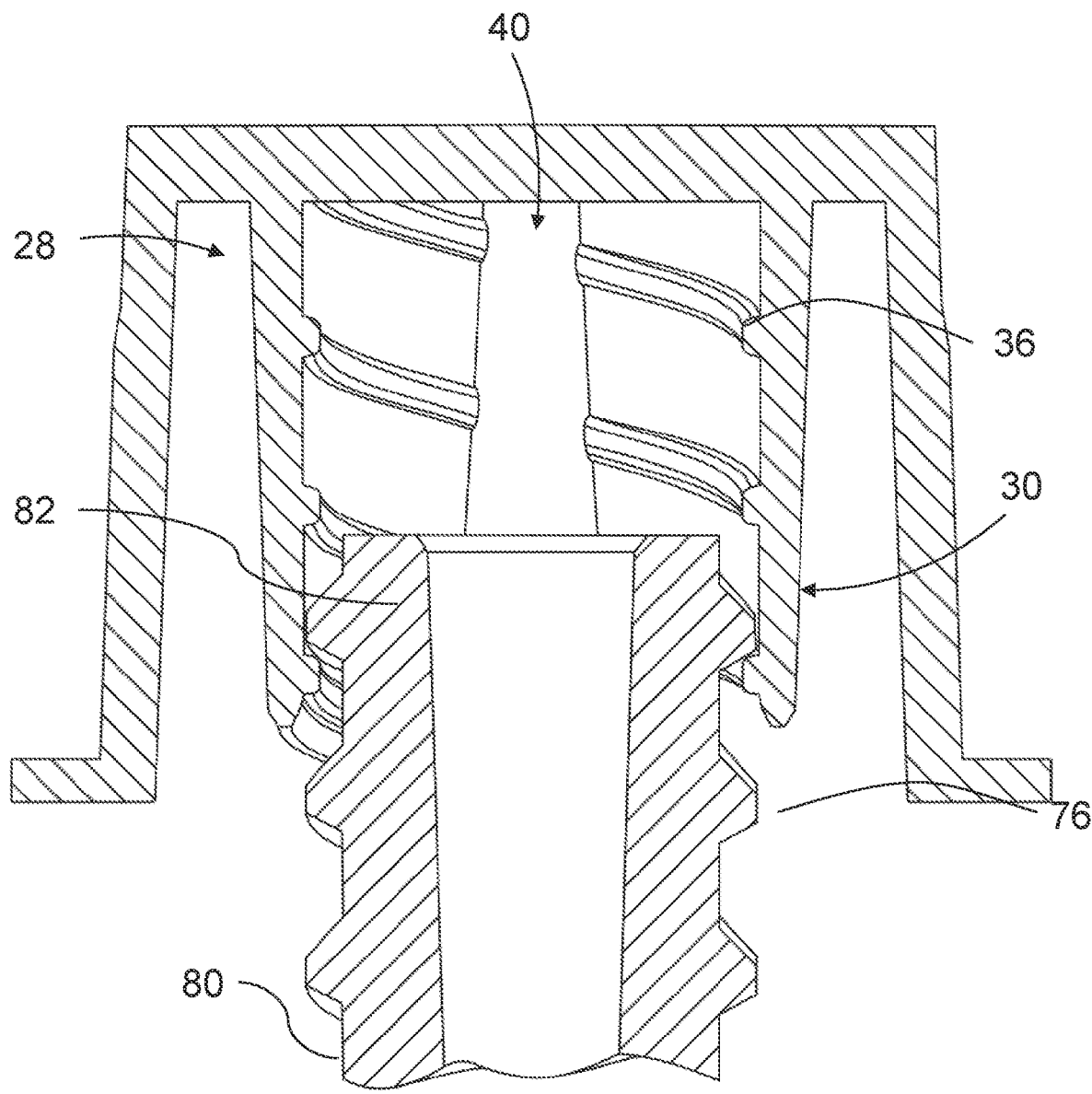

Referring further to FIG. 13, according to exemplary embodiments of the disclosure, cap 10 can receive a tip 82 of a female needleless connector 80, for example after a peelable seal (not shown) which seals first cavity 28 and second cavity 40 is removed or when the peelable seal (not shown) is pierced. The tip 82 is threadedly secured to the inner thread 36 of the protrusion 30. One or more threads 36 can be sufficient to interlock with a mating feature of a needleless connector In an exemplary implementation of FIGS. 1 and 7-11, protrusion 30 is illustrated as comprising two prongs 44 spaced by cutouts or gap 35 and extending essentially from the distal wall 25. However, also within the scope of the disclosure are caps comprising a unitary protrusion 30 without any cutouts or gaps 35, and caps having a protrusion 30 comprising any number of identical and/or different (in any dimensional characteristics, such as length width, thickness, or shape) prongs, as long as protrusion 30 is configured to engage a female connector with respect to threads 36 on its inner surface, and engage a male connector with respect to its tapered outer surface.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, cap 10 engages with male luer connectors and also with female luer connectors thereby allowing the user to clean different types of connectors with a single device, as shown in FIGS. 12 and 13. Upon mounting the cap 10 onto female luer connectors, as shown in FIG. 13, the female luer connectors is inserted into the second cavity 40 and screwed onto the threads 36 of the cap. Upon mounting the cap onto a male luer connector, as shown in FIG. 12, the male luer connector frictionally engages the outer surface of the protrusion upon insertion into the first cavity 28. Hence, the cap of the present disclosure can be mounted onto both male and female luer connectors, thus fulfilling a current need in the art.

Other aspects of the present disclosure are directed to methods of disinfecting medical connectors and assemblies. In one or more embodiments, a method of disinfecting a medical connector comprises connecting the cap of one or more embodiments to a medical connector, wherein connecting includes frictionally engaging a male medical connector onto the interior wall surface of the protrusion or upon insertion of a female medical connector into the chamber such that the female medical connector engages threads 36 and contacts the absorbent material 50 and the disinfectant or antimicrobial agent.

In one or more embodiments, an assembly comprises the cap 10 of one or more embodiments connected to a medical connector. In one or more embodiments, the medical connector is selected from a male luer connector, a female luer connector, and needleless connector.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cap comprising:
    a housing comprising
        a top wall,
        an inner cylindrical sidewall and forming a first cavity, the cavity defining a distal wall, and
        an open bottom formed by said inner cylindrical sidewall with an opening to the first cavity within said housing for receiving a hub of a female needleless connector or a male needleless connector; and
    a protrusion formed as a split-thread protrusion, the protrusion is integrally formed with the housing and positioned within said first cavity, the protrusion having an inner surface and an outer surface extending proximally from the distal wall toward the open proximal end, the inner surface of the split-thread protrusion integrally formed with the distal wall, the inner surface of the split-thread protrusion defining a second cavity,
        an inner thread on said inner surface of the protrusion, said inner thread being sufficient to interlock with a mating feature of said female needleless connector, and
        the outer surface of the protrusion being tapered from the distal wall, the taper extending in a proximal direction toward said open bottom of said housing, sized and adapted to engage the male needleless connector in a press-fit connection sufficient to interlock with a mating feature of said male needleless connector; and
    at least one absorbent material configured within said the first cavity and second cavity and a disinfectant or an antimicrobial agent retained within the absorbent material.

2. The cap of claim 1, wherein when the hub of said female needleless connector is received within said inner surface of said second cavity, said hub is secured within said inner surface of said second cavity by interlocking at least a portion of said inner surface with a mating feature on said hub of said female needleless connector.

3. The cap of claim 1, wherein said protrusion comprises one or more cantilevered prongs separated by one or more respective gaps, at least one of said cantilevered prongs configured to bend or deform to facilitate interference fit between said protrusion and said mating feature of said male needleless connector or female needleless connector.

4. The cap of claim 1, wherein said protrusion extends essentially from the distal wall of the housing toward said open bottom of said housing.

5. The cap of claim 1, wherein said protrusion extends essentially parallel to said inner sidewall of the housing.

6. The cap of claim 1, wherein an inner portion of said second cavity extends further into said housing toward said top wall than an outer portion of said second cavity.

7. The cap of claim 1, wherein the inner surface has an inclined thread pattern.

8. The cap of claim 1, wherein the inner surface has a helical-shaped thread pattern.

9. The cap of claim 1, wherein the inner surface has one or more gaps in a thread pattern.

10. The cap of claim 1, wherein said inner surface of the protrusion is essentially parallel to said outer surface of the protrusion.

11. The cap of claim 1, wherein an outer sidewall of the housing includes a plurality of grip members.

12. The cap of claim 1, wherein the female connector is selected from a group consisting essentially of needle-free connectors, catheter luer connectors, stopcocks, and hemodialysis connectors.

13. The cap of claim 1, wherein the male needleless connector is an intravenous tubing end, stopcock or male lock luer.

14. The cap of claim 1, wherein the cap comprises a polypropylene or polyethylene material.

15. The cap of claim 1, further comprising a peelable seal on an end face of the open bottom of the housing.

16. The cap of claim 15, wherein the peelable seal comprises an aluminum or multi-layer polymer film peel back top.

17. The cap of claim 15, wherein the peelable seal is heat-sealed or induction sealed to an engagement surface on the open bottom of the housing.

18. The cap of claim 1, further comprising at least one absorbent material and a disinfectant or an antimicrobial agent retained within the absorbent material.

19. The cap of claim 18, wherein the absorbent material has slits.

20. The cap of claim 18, wherein a compression of the absorbent material toward the distal wall of the housing occurs upon connection to a female luer connector.

* * * * *